United States Patent [19]

Bunin

[11] Patent Number: 5,759,491
[45] Date of Patent: Jun. 2, 1998

[54] PROCESS AND APPARATUS FOR THE DECONTAMINATION OF INFECTIOUS WASTE

[76] Inventor: Kiva Bunin, 8400 Pennsylvania Rd. #119, Bloomington, Minn. 55438

[21] Appl. No.: 505,475

[22] Filed: Jul. 21, 1995

[51] Int. Cl.⁶ .................................................. A61L 2/06
[52] U.S. Cl. .................. 422/38; 422/308; 422/309; 241/21; 241/23; 241/606; 366/107
[58] Field of Search .................. 422/32, 38, 307, 422/308, 309; 241/21, 23, 24, 46.01, 65, 606; 165/66

[56] References Cited

U.S. PATENT DOCUMENTS

| | | | |
|---|---|---|---|
| 1,653,629 | 12/1927 | Kerckhoff et al. | 165/66 |
| 2,522,796 | 9/1950 | Olson et al. | 165/66 |
| 4,542,034 | 9/1985 | Aule et al. | 165/66 |
| 4,911,836 | 3/1990 | Haggerty | 261/DIG. 75 |
| 5,054,696 | 10/1991 | Mennel et al. | 241/34 |
| 5,087,420 | 2/1992 | Jackson | 422/37 |
| 5,119,994 | 6/1992 | Placzek | 241/17 |
| 5,207,994 | 5/1993 | Suzuki et al. | 422/307 |
| 5,213,774 | 5/1993 | Noetzel | 422/309 |
| 5,217,688 | 6/1993 | Von Lersner | 422/309 |
| 5,252,290 | 10/1993 | Uesugi | 422/22 |
| 5,364,589 | 11/1994 | Buehler et al. | 422/309 |
| 5,427,737 | 6/1995 | Glazer et al. | 422/32 |
| 5,556,445 | 9/1996 | Quinn et al. | 422/209 X |

FOREIGN PATENT DOCUMENTS

| | | |
|---|---|---|
| 55-119486 | 9/1980 | Japan . |
| 0793863 | 1/1971 | U.S.S.R. . |
| 0937266 | 6/1982 | U.S.S.R. . |

*Primary Examiner*—Robert J. Warden
*Assistant Examiner*—E. Leigh McKane

[57] ABSTRACT

A process and apparatus for the decontamination of infectious waste produces a flowable influent slurry from a solid waste and aqueous liquid. The influent slurry is caused to flow through a conduit which includes a heat exchanger, a heater which brings the temperature of the slurry to at least 125 degrees C., and a convoluted holding zone which provides a residence time of at least 15 minutes for the heated slurry. In-line agitation of the slurry is accomplished by injection of pressurized gas.

20 Claims, 1 Drawing Sheet

PROCESS AND APPARATUS FOR THE DECONTAMINATION OF INFECTIOUS WASTE

BACKGROUND OF THE INVENTION

1. Field of the Invention

This invention relates generally to waste-material and, in particular, to a waste disposal system for treating and disposing of infectious or bio-hazardous waste in a manner whereby the waste is thermally treated so as to produce a non-infectious pourable stream that can be safely discharged into a sanitary sewer or landfill.

2. Description of the Prior Art

In recent years, the category of "infectious waste" has become more clearly defined as a category of environmental waste material having treatment and disposal requirements which are distinctly different from other types of non-hazardous and hazardous wastes. There has been a developing understanding that pathogenic agents which are the focus of infectious waste are transmitted primarily by blood, blood products, body fluids, bone, and tissue, and secondarily by the containers, gloves, syringes, diapers, dressings, and other objects which have come in contact with the above mentioned biological products, such objects being typical waste of hospitals, medical research facilities, and sewage systems.

Effective treatment of infectious waste requires a treatment system which is effective against bacteria and viruses as well as other potentially pathogenic agents. Proper decontamination of all of these forms of infectious waste requires a precisely controlled process whereby all pathogenic agents contained in the infectious waste are destroyed. Ideally, such a process should have the capability to be easily adjusted according to the volume and type of infectious waste being treated.

Waste treatment processes have been developed which either address certain specific types of biological or non-biological waste materials or all forms of waste generated by a particular type of generator, such as a hospital. However, such waste disposal processes have not focused exclusively on infectious waste. Therefore, such processes and systems are either not economically practicable or are otherwise unsuitable for many infectious waste generators.

In recent years waste treatment processes have been developed to provide some level of treatment of infectious waste. However, such treatment has either focused on the neutralization of bacteria only or lacked the control necessary to insure that all potentially pathogenic agents present in infectious waste, as described above, are effectively treated.

The treatment of infectious wastes with chemical disinfectants such as chlorine, is described in U.S. Pat. No. 5,087,420 and elsewhere. However, chemical disinfectants in general are unable to penetrate into the interior of particles larger than 1/16 inch suspended in a sludge, and cannot easily diffuse into hypodermic needles or sponges or other porous structures because the fine capillary passages in otherwise porous materials are blocked by trapped air bubbles. The use of chlorine has the further disadvantage of generating carcinogenic organo-chlorine compounds. Other disinfectant chemicals are either expensive, difficult to use, or of marginal effectiveness. In using a disinfectant such as chlorine, the dosage rate is uncertain because it is dependent upon the nature of the waste, its flow rate and the duration and temperature of treatment. In view of such uncertainties, batch-wise treatments with chemicals have been found preferable, as disclosed in the aforesaid U.S. Pat. No. 5,087,420.

It is accordingly an object of the present invention to provide a treatment process for rendering infectious waste non-infectious.

It is another object of this invention to provide a process as in the foregoing object which avoids the use of disinfectant chemicals and can be conducted in a continuous manner.

It is a further object of the present invention to provide a process of the aforesaid nature which can simultaneously treat solid and liquid infectious wastes.

It is still another object of this invention to provide apparatus for combining solid and liquid wastes into a pumpable slurry, and thermally treating said slurry.

It is yet another object of the present invention to produce a decontaminated slurry, separating said slurry into a solids component which is disposed of, and a liquid component which is re-cycled to produce said slurry from newly added solids component.

These objects and other objects and advantages of the invention will be apparent from the following description.

SUMMARY OF THE INVENTION

The above and other beneficial objects and advantages are accomplished in accordance with the present invention by a treatment process comprising:

a) receiving and comminuting infectious solid waste, b) blending the solid waste with an aqueous stream to produce a flowable influent slurry, c) pumping said slurry through a conduit which proceeds through a heat exchanger and terminates in a discharge port, d) heating said slurry while within said conduit in successive first, second and third stages, the temperature of said slurry being raised in each stage until a sterilizing temperature of 125° C. to 130° C. is reached, e) maintaining said slurry within said conduit for sufficient duration to achieve destruction of said infectious agents as a result of said heat treatment and thereby produce a sterilized effluent slurry, f) transferring heat from said effluent slurry to said influent slurry by way of interaction within said heat exchanger, and g) filtering said effluent slurry to produce solid and liquid phases.

The apparatus of the present invention comprises:

a) means for receiving, conveying and comminuting solid waste, b) mixing means for producing a pumpable influent slurry from comminuted solid waste and an aqueous liquid stream, c) means for receiving an aqueous stream and controllably conveying it to said mixing means, d) pumping means for forwarding said influent slurry away from said mixing means, e) conduit means which receives said influent slurry from said pumping means, said conduit means being configured to have:
  a) a heat exchanger zone comprised of adjacent upstream and downstream confining means, b) a holding zone exterior to said heat exchanger zone and comprised of convolutions preceding said downstream convolutions, and c) an exit port;

f) injection heating means which inserts heated compressed gas and/or steam into said conduit means at a site between said upstream convolutions and holding zone, and producing an effluent slurry.

g) means for controlling the pressure within said conduit means, and h) filtration means for separating said effluent slurry emergent from said exit port into liquid and solid phase components.

BRIEF DESCRIPTION OF THE DRAWING

For a fuller understanding of the nature and objects of the invention, reference should be had to the following detailed description taken in connection with the accompanying drawing forming a part of this specification and in which similar numerals of reference indicate corresponding parts in all the figures of the drawing.

DESCRIPTION OF THE PREFERRED EMBODIMENT

Figure 1:
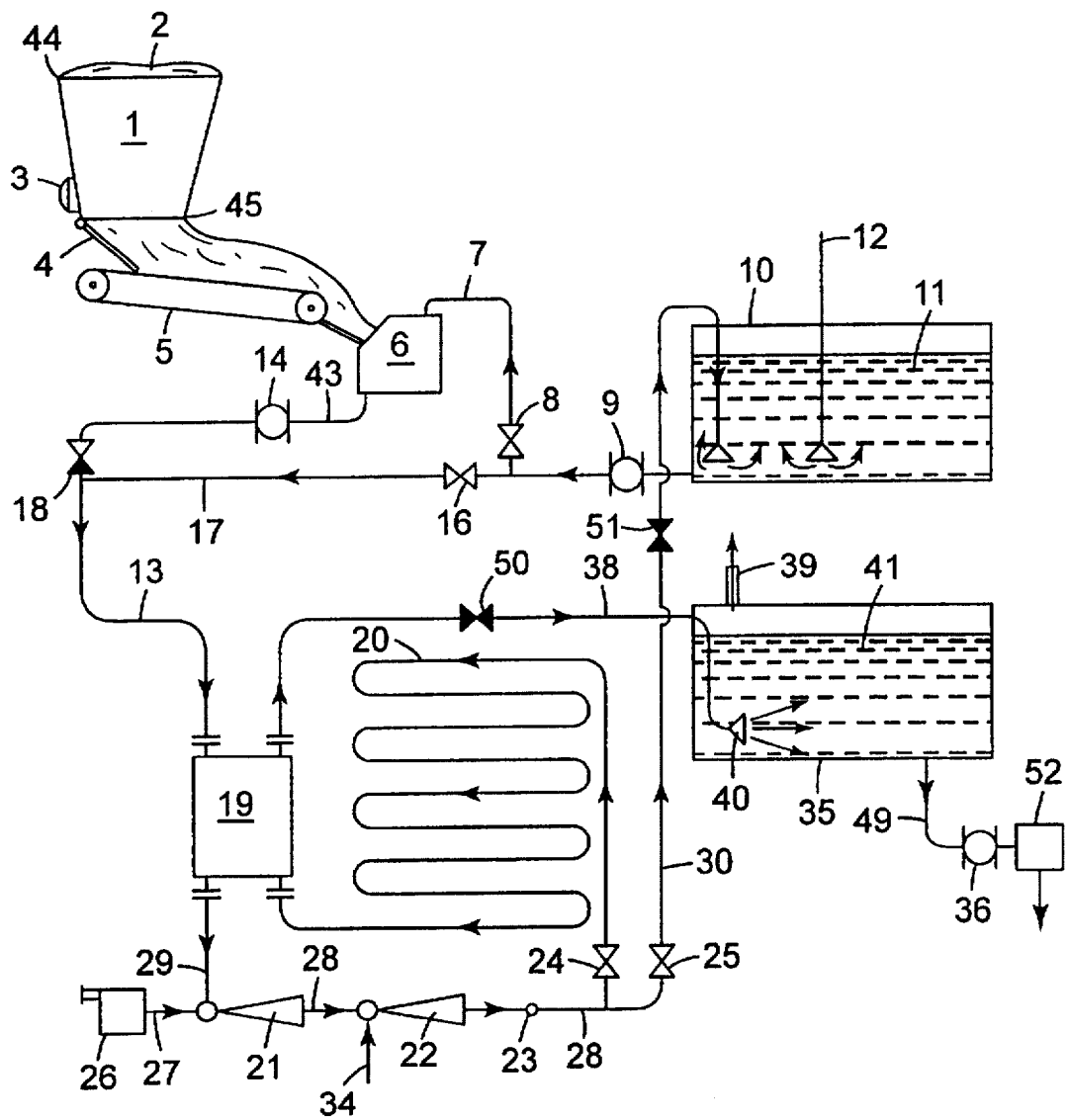
FIG. 1 is a schematic representation of an embodiment of the apparatus of the present invention.
Figure 2:
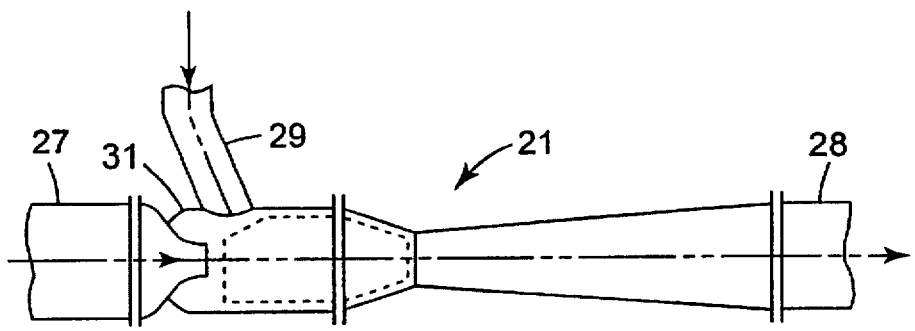
FIG. 2 is an enlarged sectional view of an embodiment of the injection component of the apparatus of FIG. 1.

Referring to FIGS. 1 and 2, an embodiment of the apparatus of this invention is shown including hopper 1 of reasonably conventional design whose cross-sectional area diminishes progressively between an uppermost extremity 44, and lowermost extremity 45. Solid waste 2 is entered into said uppermost extremity. A vibrator device 3 is attached to hopper 1 to expedite downward passage of said solid waste through said hopper. A pivoted bottom door 4 mounted upon lowermost extremity 45 controls the passage of solid waste downwardly from said hopper and onto conveyor belt 5. Solid waste falls from the end of conveyor belt 5 into grinding device 6 of conventional design equipped with intermeshing members which achieve comminution by a shredding and/or shearing principle of operation.

A tank 10 is provided for collecting an aqueous stream 11 from inlet pipe 12 which may contain infectious material such as a sewage effluent. A transfer pipe 7 communicates between tank 10 and grinding device 6. A pump 9 and supply valve 8 control the rate of passage of said aqueous stream from tank 10 to grinding device 6, thereby enabling said grinding device to produce a flowable influent slurry. An aqueous stream may also be conveyed to line 13 through valve 16 and line 17.

Conduit means in the form of pipe 13 conducts said influent slurry from said grinding device, the flow of said slurry within said pipe being controlled by pump 14 and check valve 18. Pipe 13 connects with heat exchanger 19. Said heat exchanger is comprised of an outer shell and an interior region wherein pipe 13 may be configured to have a series of convolutions designed to receive heat from a confined flow of a hotter fluid such as said slurry being returned to said heat exchanger. The heat exchanger represents a first stage of heating of the slurry. The entering influent slurry may be considered the upstream or heat-receiving fluid. Alternatively, the entering influent slurry may not be confined within a pipe within said heat exchanger but may instead fill the interior region, thereby immersing a convoluted pipe which carries a hotter downstream fluid. In either situation, the interior region of the heater exchanger may be viewed as a portion of conduit means 13. The slurry exits said heat exchanger via pipe section 29, which may be a continuation of pipe 13. The design of the heat exchanger is such as to recover up to 70% of the heat used to achieve decontamination of the slurry.

Injection heating means 21 interacts with pipe section 29 by way of the forceful injection of air heated to at least 180 degrees C., said air being supplied by compressor 26 through pipe section 27 into inlet 31. Heating means 21 represents a second stage of heating of the slurry. The injection of air further serves to provide needed agitation to the slurry, and helps propel the slurry further within pipe section 28. A second injector 22, located downstream from heating means 21, receives the heated slurry through pipe section 28. Injector 22 receives flue gases or steam through pipe 34 and introduces said gases in the downstream direction in pipe section 28. A temperature sensor 23 is located in pipe section 28 downstream from injector 22, and is adapted to control the aforesaid valves 8 and 24, and normally closed auxiliary valve 25, said valves 24 and 25 being located further downstream in the conduit means thus far comprised of pipe sections 13, 29 and 28 and heat exchanger 19.

Pipe section 20, downstream from valve 24, is configured as a holding section enveloped in thermal insulation and having a length adapted to enable the now hot slurry to maintain its highest temperature for a sufficient time of at least 15 minutes at 125 degrees C. to produce a sterilized effluent slurry. Pipe section 20 delivers said effluent slurry to heat exchanger 19 as the downstream fluid where it transfers heat to the confined heat-receiving influent slurry. An effluent pipe section 38 delivers the cooled effluent slurry 41 to holding tank 35. The arrowed lines in FIG. 1 indicate the flow path through the apparatus. A vent 39 positioned atop tank 35 transfers any noxious gaseous species to a proper disposal facility. Likewise, a bottom drain line 49 conducts the treated slurry by gravity flow or pump means 36 toward a filter 52 or an ultimate disposal site, which may be a municipal sanitary sewer system. When employed for shipboard use, the apparatus may safely discharge into the ocean.

In the event that sensor 23 determines that the temperature of the heated slurry is inadequate to achieve sterilization (namely below 125 degrees C.) it produces a diversion involving the closing of valves 24 and 8, and opening of valve 25. Such action causes the slurry to be diverted from pipe section 20 to shunt pipe 30 that returns the slurry to tank 10 for re-processing. The diversion operation also involves the closing of door 4 and stoppage of pump 14. The diversion operation is reversed when sensor 23 detects proper temperature.

It is to be noted that, when the temperature of the slurry reaches 125–130 degrees C., the autogenous pressure in the apparatus reaches approximately 30 p.s.i. Pressure-regulating valves 50 and 51 are employed to maintain said autogenous pressure.

The apparatus can also be employed with only solid waste by utilizing ordinary water instead of an aqueous sewage stream. When so employed, drain line 49 communicates with a conventional filter which separates the slurry into solid and liquid components. The solid component can be properly disposed of, whereas the liquid component can be routed back to tank 10 for re-use in the process of this invention. By virtue of the aforesaid components and their interaction, an energy-efficient apparatus is provided for the decontamination of infectious solid and/or liquid substrates.

While particular examples of the present invention have been shown and described, it is apparent that changes and modifications may be made therein without departing from the invention in its broadest aspects. The aim of the appended claims, therefore is to cover all such changes and modifications as fall within the true spirit and scope of the invention.

Having thus described my invention, what is claimed is:

1. A process for treating solid waste comprising:
   a) receiving and comminuting solid waste,
   b) blending the waste with an aqueous stream to produce a flowable influent slurry,
   c) pumping the influent slurry through conduit means,
   d) heating the influent slurry within the conduit means in successive heating stages to raise the slurry to a sterilizing temperature of at least 125° C.,
   e) agitating the slurry within the conduit means and providing a said successive heating stage by injecting pressurized and heated air into the influent slurry,
   f) maintaining the influent slurry in a holding zone comprising convolutions in the conduit means downstream from the site of injecting pressurized air to lengthen the time of the heat treatment, and
   g) conveying to a discharge port the effluent slurry that leaves the holding zone.

2. The process of claim 1 wherein said time of the heat treatment is at least 15 minutes.

3. The process of claim 1 wherein said effluent slurry is filtered after leaving the holding zone to produce solid and liquid phases, said liquid phase being recycled as the aqueous stream that produces said influent slurry.

4. The process of claim 1 wherein a portion of the conduit means carrying the influent slurry and a portion of the conduit means carrying the effluent slurry pass through a heat exchanger where heat from the effluent slurry is transferred to the influent slurry.

5. The process of claim 1 wherein, downstream from the site of said injecting pressurized and heated air into the influent slurry, additional gas heated to an elevated temperature is injected into the influent slurry in the conduit means, and imparts heat to the influent slurry to elevate the influent slurry in temperature.

6. The process of claim 5 wherein the additional heated gas is introduced at a downstream site adjacent to the site where heated and pressurized air is introduced.

7. The process of claim 5 wherein the heated and pressurized air is introduced into the conduit means on a path aligned with the longitudinal axis of the downstream conduit means; and the additional heated gas is introduced at a downstream site adjacent to the site where heated and pressurized air is introduced.

8. The process of claim 7 wherein influent slurry is conveyed to the site of introduction of heated and pressurized air on a path at an angle to the path on which air is produced.

9. The process of claim 1 wherein the heated and pressurized air is introduced into the conduit means on a path aligned with the longitudinal axis of the downstream conduit means.

10. The process of claim 9 wherein influent slurry is conveyed to the site of introduction of heated and pressurized air on a path at an angle to the path on which air is introduced.

11. Apparatus for the decontamination of solid waste comprising:
    a) means for comminuting solid waste,
    b) means for controllably conveying an aqueous stream to the comminuting means, where the comminuted solid waste and aqueous stream are blended to form a pumpable influent slurry,
    c) pumping means for forwarding the influent slurry away from the comminuting means,
    d) conduit means which receives the influent slurry from the pumping means and which includes a heat exchanger zone, a holding zone, and an exit port,
    e) injection heating means which injects heated pressurized air into a pipe section of the conduit means at a site between the heat exchanger zone and the holding zone, the conduit means in the holding zone being convoluted to have a length sufficient for slurry conveyed through the conduit means to be held for a sufficient time to be sterilized, and the conduit means being routed to convey the sterilized effluent slurry through the heat exchanger zone to the exit port.

12. Apparatus of claim 11 which includes a site for injection of heated gas into the conduit means between the heat exchanger zone and the holding zone in addition to the site for injection of heated, pressurized air.

13. The apparatus of claim 11 further comprising (a) means for monitoring the temperature of the influent slurry between the site where heated pressurized air is injected and the holding zone, and (b) a diversion circuit comprising valves located between the temperature monitoring means and holding zone, and a secondary conduit connected from the valves to the means for controllably conveying an aqueous stream to the comminuting means, the valves being automatically responsive to the temperature monitoring means, whereby slurry is diverted from the conduit means before the holding zone and conveyed to the means for controllably conveying an aqueous stream to the comminuting means.

14. Apparatus of claim 11 wherein the heated and pressurized air is introduced into the pipe section of the conduit means on a path aligned with the longitudinal axis of the downstream pipe section.

15. Apparatus of claim 14 wherein the conduit means for conveying influent slurry to the site of introduction of heated and pressurized air is at an angle to the path on which air is introduced.

16. Apparatus of claim 15 which includes a site for introduction of heated gas into the conduit means immediately downstream from the site for injection of heated, pressurized air.

17. A process for treating solid waste comprising:
    a) receiving and comminuting solid waste,
    b) blending the comminuted waste with an aqueous stream to produce a flowable influent slurry stream,
    c) pumping the influent slurry stream through conduit means,
    d) heating the influent slurry stream within the conduit means in successive heating stages to raise the slurry to a sterilizing temperature of at least 125° C.,
    e) agitating the influent slurry stream within the conduit means and providing a said successive heating stage by injecting pressurized and heated air into the influent slurry stream after the first of the heating stages,
    f) injecting additional gas comprising steam or flue gas into the influent slurry stream in the conduit means to further elevate the slurry in temperature, g) maintaining the influent slurry stream in a holding zone comprising convolutions in the conduit means downstream from the sites of injecting pressurized air and additional heated gas to lengthen the time of the heat treatment, and h) conveying to a discharge port the effluent slurry stream that leaves the holding zone.

18. The process of claim 17 wherein the steam or flue gas is introduced at a downstream site adjacent to the site where heated and pressurized air is introduced.

19. The process of claim 18 wherein the heated and pressurized air is introduced into the conduit means on a path aligned with the longitudinal axis of the downstream conduit means.

20. The process of claim 19 wherein influent slurry is conveyed to the site of introduction of heated and pressurized air on a path at an angle to the path on which air is introduced.

* * * * *